US00PP30149P2

(12) United States Plant Patent
Theiss

(10) Patent No.: US PP30,149 P2
(45) Date of Patent: Jan. 29, 2019

(54) ***HIBISCUS* PLANT NAMED 'THEISSHSSTL'**

(50) Latin Name: *Hibiscus syriacus*
Varietal Denomination: THEISSHSSTL

(71) Applicant: Daryl Theiss, Normangee, TX (US)

(72) Inventor: Daryl Theiss, Normangee, TX (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,746

(22) Filed: Dec. 21, 2017

(51) Int. Cl.
*A01H 5/02* (2018.01)

(52) U.S. Cl.
USPC ..... Plt./257
CPC ..... *A01H 5/02* (2013.01)

(58) Field of Classification Search
USPC ..... Plt./257
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct *Hibiscus* cultivar named 'THEISSHSSTL' is disclosed, characterized by distinctive cream and green variegated foliage. Plants are upright and compact with lavender double flowers. The new variety is a *Hibiscus*, normally produced as an outdoor garden or container plant.

2 Drawing Sheets

Latin name of the genus and species: *Hibiscus syriacus*.
Variety denomination: 'THEISSHSSTL'.

BACKGROUND OF THE INVENTION

The new *Hibiscus* cultivar is a product of chance discovery. The inventor discovered the new variety as a naturally occurring single branch mutation. The parent variety is an unpatented, unnamed *Hibiscus syriacus* having double flowers. The inventor selected the new variety in May 2008 at a farm in Humble, Tex.

The inventor observed this branch sport during the Summer, then selecting it for confidential propagation and testing.

Asexual reproduction of the new cultivar 'THEISSHSSTL' was first performed in September of 2008 at a research nursery in Grand Haven, Mich. by vegetative soft wood cuttings. Subsequent propagation has shown that the unique features of this cultivar are stable and reproduced true to type in multiple successive generations.

SUMMARY OF THE INVENTION

The cultivar 'THEISSHSSTL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'THEISSHSSTL' These characteristics in combination distinguish 'THEISSHSSTL' as a new and distinct *Hibiscus* cultivar:

1. Compact plant habit
2. Stable foliage variegation.
3. Double lavender flowers.

PARENT COMPARISON

Plants of the new cultivar 'THEISSHSSTL' are similar to plants of the parent in most horticultural characteristics, however, plants of the new cultivar 'THEISSHSSTL' differ in the following;

1. The new variety is compact; parent is a larger plant.
2. The new variety has variegated foliage; parent has green leaves.

COMMERCIAL COMPARISON

Plants of the new cultivar 'THEISSHSSTL' can be compared to the variety *Hibiscus syriacus* 'America Irene Scott', U.S. Plant Pat. No. 20,579. These varieties are similar in most horticultural characteristics however, 'THEISSHSSTL' differs in the following:

1. The new variety has lavender flowers; comparator has pink flowers.
2. The new variety is variegated with green leaves; comparator is variegated with blue-green leaves.
3. New variety has more cream variegation; comparator has narrower cream variegation, mostly on edges of leaves.

BRIEF DESCRIPTION OF THE PHOTOGRAPHS

Figure 1:
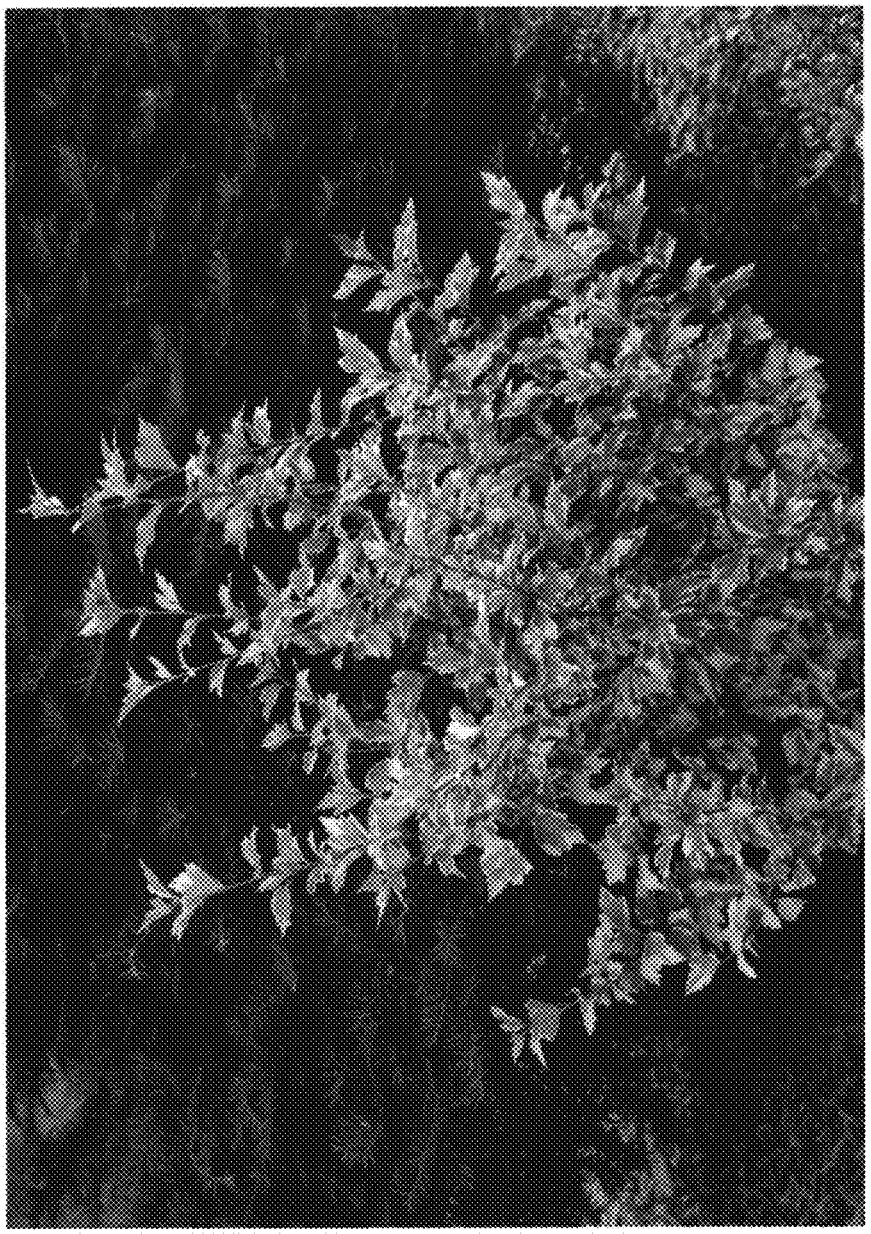

The accompanying photograph in FIG. 1 illustrates in full color a typical plant of 'THEISSHSSTL' grown in the ground outdoors in Grand Haven, Mich.

Figure 2:
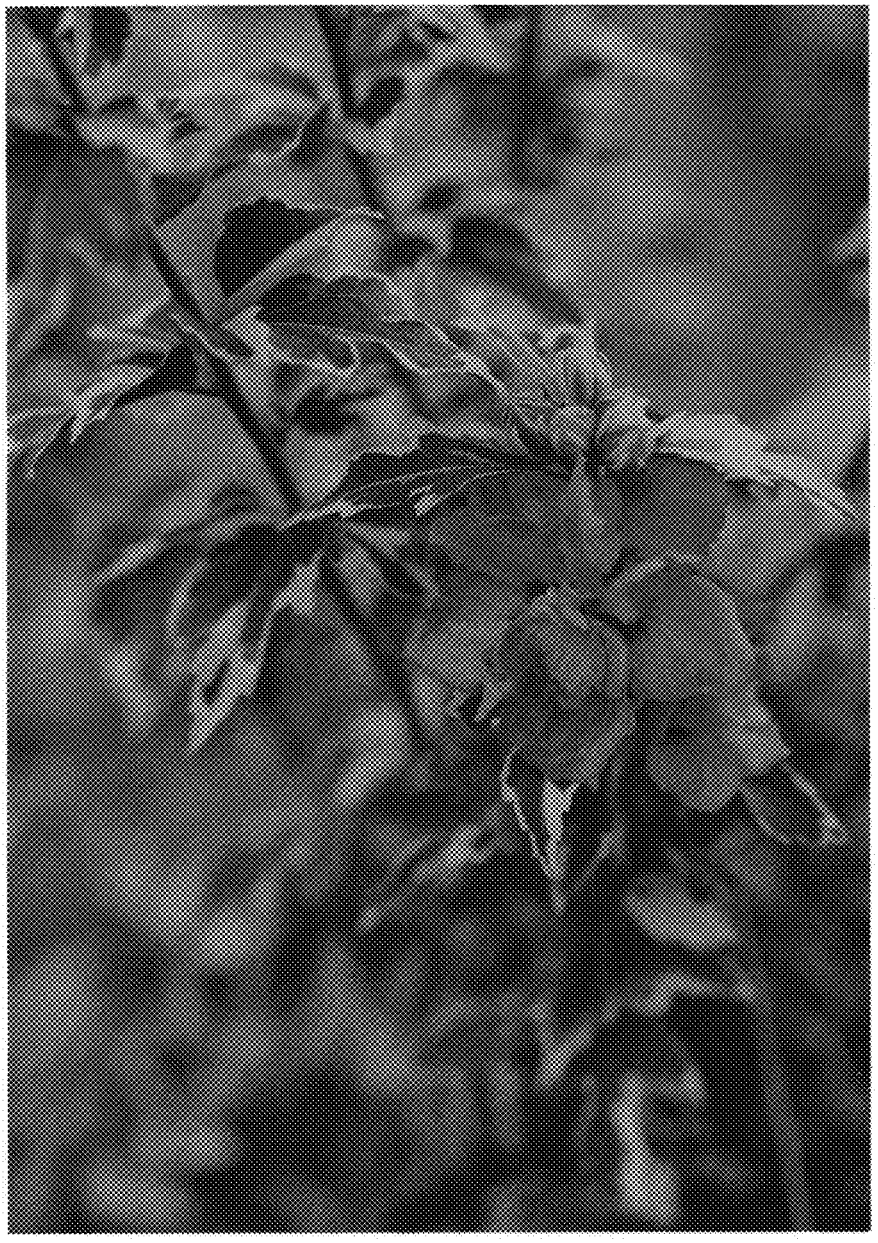

FIG. 2 illustrates in full color a typical flower and foliage of 'THEISSHSSTL'. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'THEISSHSSTL' plants grown in a polyhouse in Grand Haven, Mich. Measurements were taken during the July of 2017. The plants were 2 years old in 3 gallon containers. The growing temperature ranged from approximately 18° C. to 27° C. during the day and 5° C. to 10° C. Measurements and numerical values represent averages of typical plant types.

Botanical classification: *Hibiscus syriacus* 'THEISSHSSTL'.

PROPAGATION

Time to initiate roots: 20 days at approximately 25° C.

Root description: Fibrous, medium root thickness. Tan/brown in color, not effectively measured with a color chart.

Time to produce a rooted young plant: About 90 days at 25° C.

PLANT

Plant type: Perennial flowering shrub.

Age of plant described: Approximately 2 years old.

Growth habit: Upright, spreading outward at mostly acute angles.

Pot size of plant described: 3 gallon pot.

Height: 23 cm.

Plant spread: 19 cm.

Plant vigor: Good.

Length of primary lateral branches: 20 cm.

Diameter of lateral branches: 9 mm.

Quantity of lateral branches: 4-5.

Stem:

*Stem shape*.—Round.

*Stem strength*.—Strong.

*Color*.—Greyed-brown 199C.

*Angle of attachment*.—Acute, less than 45 degrees from center.

Internode length: 1.5 cm.

FOLIAGE

Leaf:

*Arrangement*.—Whorled.

*Leaf shape*.—Ovate.

*Average length*.—5-6 cm.

*Average width*.—4-5 cm.

*Apex*.—Acuminate.

*Base*.—Obtuse.

*Margin*.—Lobed.

*Texture of top surface*.—Smooth with rough venation.

*Texture of bottom surface*.—Smooth with rough venation.

*Color*.—Young foliage upper side: Greyed-Yellow 160A and Greyed-Yellow 160B. Young foliage under side: Greyed-Yellow 160A and Greyed-Yellow 160B. Mature foliage upper side: Margin: Greyed-Yellow 160A and Greyed-Yellow 160B. Interior: Yellow-Green 147C and Green 137B. Mature foliage under side: Margin: Greyed-Yellow 160A and Greyed-Yellow 160B. Interior: Yellow-Green 147C and Green 137B.

*Venation*.—Pattern: Pinnate. Venation coloration: Color upper side: Yellow-Green 147C and Green 137B. Color under side: Yellow-Green 147B and Yellow-Green 147C.

*Petiole*.—Average Length: 7-13 mm. Diameter: 1 mm. Petiole color upper side: Yellow-Green 146C. Petiole color lower side: Yellow-Green 146C. Petiole Texture upper side: Pubescent. Petiole Texture lower side: Waxy.

FLOWER

Natural flowering season: Mid-Summer.

Flowering form: Solitary rotate flowers. Axillary occurring.

Quantity of flowers per plant: About 20.

Flower aspect: Outward facing.

Size:

*Height*.—4 cm.

*Diameter*.—6 cm.

Flower other characteristics:

*Persistence*.—Self-cleaning.

*Fragrance*.—Earthy.

Bud:

*Shape*.—Round.

*Length*.—1.5 cm.

*Diameter*.—1 cm.

*Color*.—Yellow-Green 153A and Yellow-Green 146B.

Petal:

*Petal arrangement*.—Rotate with center petaloids.

*Number of petals per flower*.—5.

*Fused*.—No.

*Petal shape*.—Obovate.

*Petal base*.—Truncate.

*Margin*.—Sinuate.

*Tip shape*.—Obtuse.

*Length*.—2 cm.

*Width*.—2 cm.

*Texture*.—Upper: Smooth. Lower: Smooth.

*Appearance*.—Delicate, with slightly matte appearance upper and lower surfaces.

Petal color:

*When opening*.—Upper surface: Mix of Purple-Violet N81A and White 155A. Lower surface: Mix of Purple-Violet N81A and White 155A.

*Fully opened*.—Upper surface: Purple Violet N81C with eye in center Red-Purple 63A. Lower surface: Purple Violet N81C and Purple-Violet N82A.

*Fading to*.—No significant change observed.

Petaloids:

*Arrangement*.—Ruffled in flower center.

*Number of per flower*.—On average 25.

*Fused*.—No.

*Petal shape*.—Highly irregular obovate.

*Petal base*.—Truncate.

*Margin*.—Mostly entire.

*Tip shape*.—Obtuse or acute, irregular shapes.

*Length*.—2.5 cm.

*Width*.—5 to 12.5 mm.

*Texture*.—Upper: Smooth. Lower: Smooth.

*Appearance*.—Somewhat matte appearance upper and lower surfaces.

Petaloid color:

*When opening*.—Upper surface: Violet N81C with eye in center Red-Purple 63A. Lower surface: Purple Violet N81C and Purple-Violet N82A.

*Fully opened*.—Upper surface: Violet N81C with eye in center Red-Purple 63A. Lower surface: Purple Violet N81C and Purple-Violet N82A.

Sepal:

*Arrangement*.—Whorl.

*Number*.—Average 7.

*Shape*.—Aricular.
*Tip*.—Acute.
*Base*.—Fused.
*Margin*.—Entire.
*Length*.—1.5 cm.
*Width*.—2 mm.
*Texture, upper*.—Glabrous.
*Texture, lower*.—Glabrous.
*Color*.—Mature: Upper surface: Near Yellow-Green 147C and Green 137B. Under surface Near Yellow-Green 147C and Green 137B.

Calyx:
*Shape*.—Funnelform.
*Length*.—4.0 cm.
*Diameter*.—4.0 cm.

Peduncle:
*Length*.—1.2 cm.
*Diameter*.—2 mm.
*Color*.—Near Greyed-Yellow 160A.
*Orientation*.—About 45°, or less.
*Strength*.—Moderate.
*Texture*.—Smooth, waxy.

REPRODUCTIVE ORGANS

Stamens:
*Number*.—Average 15, clustered and implanted in style, typical of *Hibiscus*.
*Filament length*.—2.5 mm.
*Filament color*.—Near RHS White N155D.

Anthers:
*Shape*.—Dorsifixed.
*Length*.—2 mm.
*Color*.—Near RHS Orange-White 159A.
*Pollen color*.—Near RHS Yellow 11B.
*Pollen amount*.—Moderate.

Pistil:
*Number*.—1.
*Length*.—3.9 cm.
*Style*.—Length: 3.7 cm. Color: Near RHS White N155D.
*Stigma*.—Shape: Club-shaped. Color: Near RHS White 155B.
*Ovary color*.—Near Yellow-green; 150C, ovary completely covered by the base of the pistil style.

OTHER CHARACTERISTICS

Seeds and fruits: Not observed to date.
Disease/pest resistance: Neither resistance nor susceptibility to normal diseases and pests of *Hibiscus syriacus* have been observed.
Garden performance: Good tolerance for wind and rainy conditions.
Temperature tolerance: Low temperature tolerance to −26° C., high temperature tolerance to 35° C.

What is claimed is:

1. A new and distinct cultivar of *Hibiscus* plant named 'THEISSHSSTL' as herein illustrated and described.

* * * * *